(12) United States Patent
Campagne et al.

(10) Patent No.: US 10,036,633 B2
(45) Date of Patent: Jul. 31, 2018

(54) DEVICE FOR THE ROBOTIC CONTROL OF A STRUCTURE BY ULTRASOUND-LASER

(71) Applicant: AIRBUS SAS, Blagnac (FR)

(72) Inventors: Benjamin Campagne, Saint-Herblain (FR); Hubert Voillaume, Issy-les-Moulineaux (FR)

(73) Assignee: AIRBUS SAS, Blagnac (FR)

( * ) Notice: Subject to any disclaimer, the term of this patent is extended or adjusted under 35 U.S.C. 154(b) by 265 days.

(21) Appl. No.: 14/897,128

(22) PCT Filed: Jun. 13, 2014

(86) PCT No.: PCT/EP2014/062403
§ 371 (c)(1),
(2) Date: Dec. 9, 2015

(87) PCT Pub. No.: WO2014/198910
PCT Pub. Date: Dec. 18, 2014

(65) Prior Publication Data
US 2016/0131475 A1    May 12, 2016

(30) Foreign Application Priority Data

Jun. 14, 2013  (FR) ..................................... 13 55582

(51) Int. Cl.
*G01B 17/06* (2006.01)
*G01N 29/04* (2006.01)
(Continued)

(52) U.S. Cl.
CPC ........... *G01B 17/06* (2013.01); *G01N 29/041* (2013.01); *G01N 29/225* (2013.01);
(Continued)

(58) Field of Classification Search
None
See application file for complete search history.

(56) References Cited

U.S. PATENT DOCUMENTS

| 6,687,328 B2 * | 2/2004 | Bavendiek ............. G01N 23/04 378/208 |
| 2008/0291963 A1 * | 11/2008 | Deaton, Jr. ........ G01N 29/2418 372/69 |

(Continued)

FOREIGN PATENT DOCUMENTS

| DE | 10259653 | 4/2004 |
| WO | 2012110492 | 8/2012 |

OTHER PUBLICATIONS

International Search Report, International Application No. PCT/EP2014/062403, dated Sep. 30, 2014.

*Primary Examiner* — Paul West
*Assistant Examiner* — Mark A Shabman
(74) *Attorney, Agent, or Firm* — Greer, Burns & Crain, Ltd.

(57) ABSTRACT

The device according to the invention consists of associating a laser inspection head including a source emitting a laser beam swept along a defined axis and a handling robot seeing to the movement and spatial orientation of parts whose structure requires inspection. The inspection head and the handling robot are configured and arranged across from one another such that the inspection head occupying a stationary position, the handling robot can move the part to be inspected across from the inspection head, such that the sweep of the laser beam combined with the movement of the part in a direction perpendicular to the sweeping direction makes it possible to inspect the entire surface of the part. In one particular configuration, the handling robot makes it possible to vary the orientation of the part relative to the direction of the laser beam so as to have optimal lighting of the part.

9 Claims, 3 Drawing Sheets

(51) Int. Cl.
*G01N 29/24* (2006.01)
*G01N 29/275* (2006.01)
*G01N 29/22* (2006.01)

(52) U.S. Cl.
CPC ....... *G01N 29/2418* (2013.01); *G01N 29/275* (2013.01); *G01N 2291/0231* (2013.01)

(56) References Cited

U.S. PATENT DOCUMENTS

| | | |
|---|---|---|
| 2012/0098961 A1 | 4/2012 | Handa et al. |
| 2012/0111115 A1* | 5/2012 | Ume .................. G01N 29/2418 73/588 |
| 2012/0263347 A1 | 10/2012 | Ichimaru |
| 2012/0320383 A1* | 12/2012 | Dubois ................ G01N 29/043 356/502 |
| 2013/0342846 A1 | 12/2013 | Campagne et al. |

* cited by examiner

Balayage n

Balayage n+1

DEVICE FOR THE ROBOTIC CONTROL OF A STRUCTURE BY ULTRASOUND-LASER

CROSS REFERENCE TO RELATED APPLICATIONS

This application is the National Stage of International Application No. PCT/EP2014/062403 having an International Filing Date of 13 Jun. 2014, which designated the United States of America, and which International Application was published under PCT Article 21 (s) as WO Publication 2014/198910 A1 and which claims priority from, and the benefit of, French Application No. 1355582 filed on 14 Jun. 2013, the disclosures of which are incorporated herein by reference in their entireties.

BACKGROUND

1. Field

The presently disclosed embodiment relates to the general field of ultrasonic inspection of the manufacturing quality of aeronautical system parts, especially composite parts, and more particularly to the inspection of the material health of such parts by laser-ultrasound.

2. Brief Description of Related Developments

The analysis of the material health of structural elements is at the present time carried out by laser-ultrasound, which is a contactless inspection method that is very suitable for parts of complex shape.

It will be recalled here that analysis of material health consists in searching for defects, delaminations, shrink marks, pores, cracks or other anomalies that may be found in materials used to manufacture mechanical parts, especially structural elements.

To meet the need for high-throughput inspection of parts, the current tendency is to entrust the execution of integrity tests to automatic systems, in other words robots. The execution of these tests by robots especially makes it possible, in the context of tests on mass-produced parts, to ensure an excellent reproducibility of the tests from one part to the next.

From a structural point of view, these robots are generally equipped with an arm, or more generally a movable appendage, terminating in a laser source. Especially in the case of inspection of large parts, these robots may furthermore be configured so as to be able to move so as to position themselves in proximity to the part.

In certain existing installations, the parts to be inspected are held stationary during the inspection. The robot moves the inspecting head over the part, and hence it is the inspecting head, and not the part, that moves. This is in particular the case for installations intended to test large parts.

Depending on the circumstances, the laser source may then be a stationary beam source, the integrity test then being carried out by moving the inspecting head so that it illuminates in succession a set of points distributed over the surface of the part that it is desired to inspect. In such a configuration, the part is inspected by operating the robot in a dynamic mode. The surface is thus scanned by moving the robot, or at least the inspecting head, relative to the surface to be inspected.

Alternatively, the laser source may also be a moving beam source. In this second case, the source is itself equipped with optical means, mirrors for example, allowing, to a certain extent, the laser beam produced to be deflected about one or two axes. Thus, the integrity test is carried out by positioning the source in succession facing the part at various points that are spaced apart from each other, and by scanning a surface portion with the laser beam emitted by the source so that said beam covers a given zone of the surface of the part. The number and arrangement of the inspection points are defined such that during the test the entirety of the surface of the part is scanned by the laser beam. Such a configuration is especially used in the LUCIE (acronym of "Laser Ultrasonics Composite inspection Equipment") system developed by the Applicant.

In contrast, in other existing installations the robot includes a stationary inspecting head with a stationary laser beam source and it is the parts to be inspected that are moved and passed in front of the inspecting head. It is then the movement of the inspected part that makes it possible for the inspecting head to scan the entire surface of the part. In such installations the part may for example be moved by a handling arm that picks up the part and moves it facing the inspecting head. Such installations have the advantage of being simple and robust, insofar as, since the inspecting head remains stationary, it is easier to supply the laser source with power than would be the case if the same source were mobile. The handling arm here serves only to move the inspected part. This simplicity is moreover amplified if the laser source used emits a stationary beam. In contrast, to inspect the entirety of the part the handling arm must be able to precisely position the part relative to the inspecting head, and be able to rapidly more the latter.

Although these two types of installation are generally very suitable for the type of integrity inspections currently carried out by robots, there are however cases where they lead to limitations, especially in terms of the rapidity of inspection execution or even in terms of the effectiveness of the tests performed. In particular, such installations are generally not very appropriate for the inspection of the integrity parts having irregular surfaces, with more or less marked reliefs, and/or a complex geometry.

SUMMARY

One aim of the presently disclosed embodiment is to provide a means allowing operational constraints on existing robotic installations for inspecting parts to be overcome, in particular in the context of testing of the structural integrity of aeronautical parts.

For this purpose, the subject of the presently disclosed embodiment is a device for inspecting the structure of a composite part including an inspecting head itself including a source emitting at least one laser beam, and a handling robot configured to hold the part and move the surface of said part relative to the inspecting head in such a way that said surface is able to be scanned by the laser beam emitted by the source with which the inspecting head is equipped. Said laser source includes means for scanning the emitted laser beam along a given scanning axis and with a given scanning amplitude. The handling robot is configured in order to be able to move the surface of the part along an axis substantially perpendicular to the axis along which the laser beam moves.

According to various arrangements that may optionally be used conjointly:

the laser source emitting two laser beams, it comprises means allowing the two beams to be scanned along two parallel axes.

the laser source emitting two laser beams, the means for scanning the two laser beams are configured so that each beam is scanned independently of the other.

the handling robot is configured in such a way that after each scan by the laser source, the surface of the part is moved relative to the inspecting head in such a way that the following scan covers a zone of the surface of the part as yet not scanned thereby.

the laser source emitting two laser beams, the motional step, d', of the part after each scan and the separation between the two laser beams is defined so as to obtain a complete scan of the surface of the part with the desired resolution.

the handling robot is configured so as to allow the surface of the inspected part to be orientated relative to the inspecting head in such a way that at every inspection point on the surface of the part the laser beam has an incidence that is optimal in illumination terms.

the handling robot includes means for gripping the part, which means are capable of making the surface of the part pivot about two substantially perpendicular axes.

the handling robot consists of a translating element on which the parts to be inspected are placed, which ensures a linear movement of said parts. Said element is arranged relative to the inspecting head in such a way that the part to be inspected moves along an axis substantially perpendicular to the scanning axis of the laser beam.

the handling robot consisting of a translating element, it is configured in such a way that, during the inspection operation, each part to be inspected can be brought, via a continuous movement of the translating element, into proximity with the inspecting head, then moved stepwise between two successive scans under the laser source.

the handling robot consists of a rotating element on which the part to be inspected is placed and ensuring a rotation of said part about itself, said element being arranged relative to the inspecting head in such a way that the faces of the part to be inspected are scanned in succession by the laser beam of the inspecting head.

BRIEF DESCRIPTION OF THE DRAWINGS

Features and advantages of the presently disclosed embodiment will be better appreciated by virtue of the following description, which makes reference to the appended figures, in which.

DETAILED DESCRIPTION

Whatever the envisioned aspect, the essential feature of the device according to the presently disclosed embodiment is to combine an inspecting head using a mobile laser beam, and means for holding the inspected part and moving this part facing the inspecting head in such way that the entirety of the surface of the part can be illuminated by the beam during the test.

According to the presently disclosed embodiment, the laser source includes means allowing the laser beam to be deflected along a single axis, so as to perform a mono-axial scan. This deflection, which is advantageously simple to implement, may be carried out by any known means, for example by a mirror that is rotatable relative to the emission direction of the laser beam.

Also according to the presently disclosed embodiment, the means for holding and moving the inspected part are configured so as to be able, during the inspection, to move the part facing the inspecting head, in a direction substantially perpendicular to the scanning direction of the laser beam.

Figure 1A:
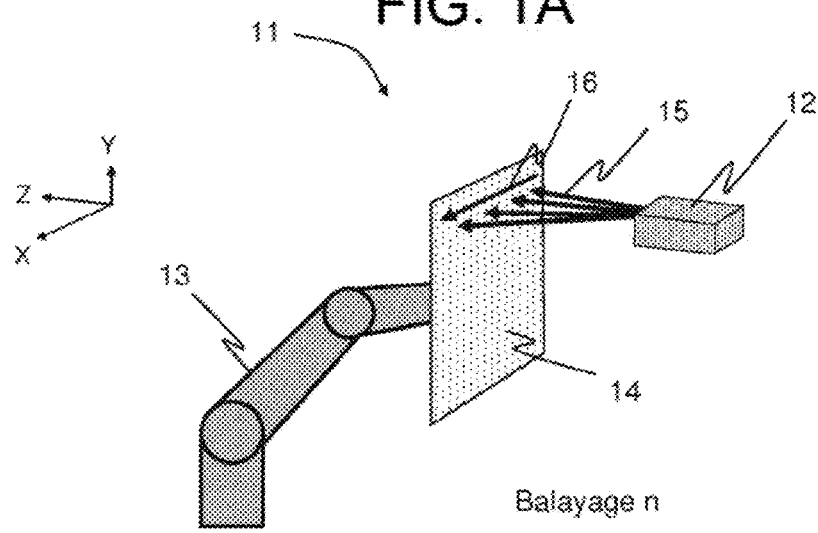
FIGS. 1A and 1B are schematic representations of the device according to a first aspect of the presently disclosed embodiment.
Figure 1B:
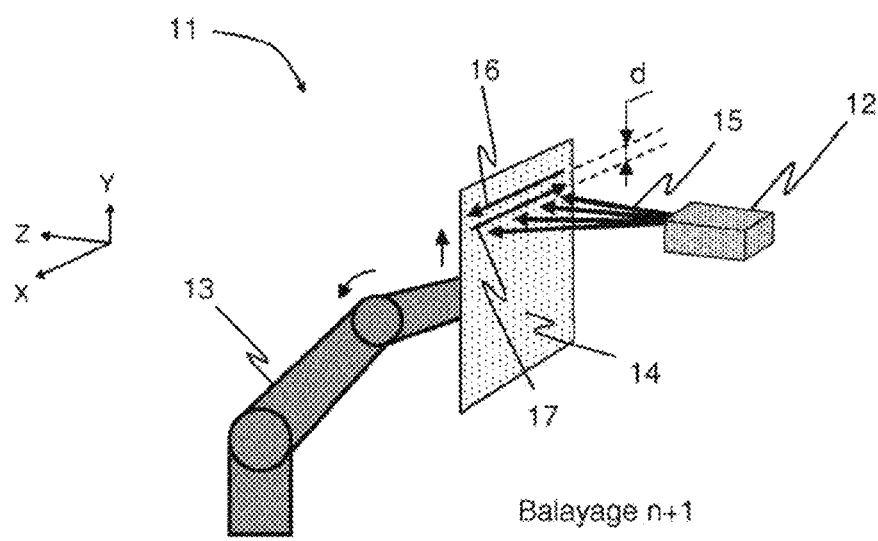

FIGS. 1A and 1B show, by way of nonlimiting examples, a first aspect of the device according to the presently disclosed embodiment.

In this aspect, the device 11 here includes an inspecting head 12 including a single-beam laser source and a robot 13 equipped with a handling arm, which holds the part 14 and positions and orients it facing the head 12. The use of a handling robot here advantageously allows the part 14 to be moved, relative to the inspecting head 12, independently along three axes X, Y and Z. It is thus possible to position the part 14 as desired relative to the inspecting head 12.

Consequently, the inspection of a part 14 consists, for example, from an initial position of the part relative to the inspecting head 12, in deflecting the laser beam 15 so that it scans the part along a line parallel to the K-axis, which line is represented by the arrow 16, then, when the maximum deflection of the beam is reached, in moving the part 14 a distance d along the Y-axis perpendicular to the X-axis and in deflecting the laser beam 15 in the opposite direction so that it scans the part along a line parallel to the preceding scanning line and distant therefrom by a step distance d, which line is represented by the arrow 17.

Alternatively, to inspect the part 14, it is of course possible, after each movement d, to scan the laser beam in a single direction corresponding to the direction of the arrow 16 or of the arrow 17.

It will be noted here that the motional step, d, of the part after each scan is defined so as to obtain a complete scan of the surface of the part 14 with the desired resolution.

It is thus possible, by combining the scan of the laser beam 15 with a gradual linear movement of the part 14 along the Y-axis, to carry out a gradual inspection, line by line, of all the surface of the part 14.

Such a methodology advantageously allows inspection time to be optimized insofar as, during the duration of a scan, the inspected part is in a stationary position and as synchronization between the laser emission and the movement of the part 14 facing the inspecting head 12 is necessary only at the moment of the line change.

Figure 2:
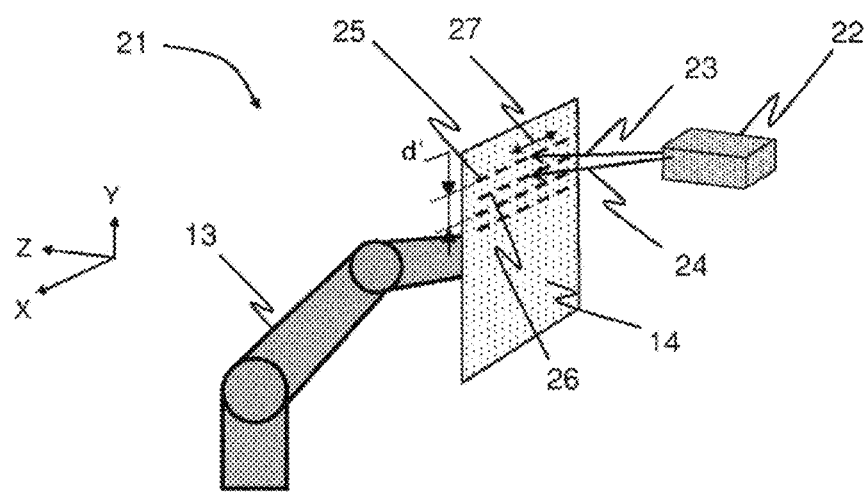
FIG. 2 is a schematic representation of the device according to a second aspect of the disclosed embodiment

FIG. 2 shows, also by way of nonlimiting example, a second aspect of the device according to the presently disclosed embodiment.

In this aspect, the device 21 here includes an inspecting head 22 including a laser source emitting two beams 23 and 24, and a handling robot 13 that holds the part 14 and positions and orients it facing the head. In this second aspect, the laser source includes means allowing the laser beams 23 and 24 to be deflected along two parallel axes, represented by the dotted lines 25 and 26, so as to carry out a mono-axial scan with each of the two beams, the beams 23 and 24 being able to be deflected in two directions as illustrated by the double arrow 27. Depending on the variant aspect in question, the means allowing the two laser beams to be deflected are configured either to perform a simultaneous scan of the two beams or to perform two independent scans.

In comparison with the aspect in FIGS. 1A and 1B, this second aspect advantageously allows the surface of the part 14 to be explored twice as fast, the movement, d', of the part 14 between two consecutive scans then preferably being equal to two time the step distance d used in the case of a single-beam scan.

It will be noted here that the motional step, d' of the part after each scan and the separation between the two laser beams are defined so as to obtain a complete scan of the surface of the part 14 with desired resolution.

Figure 3:
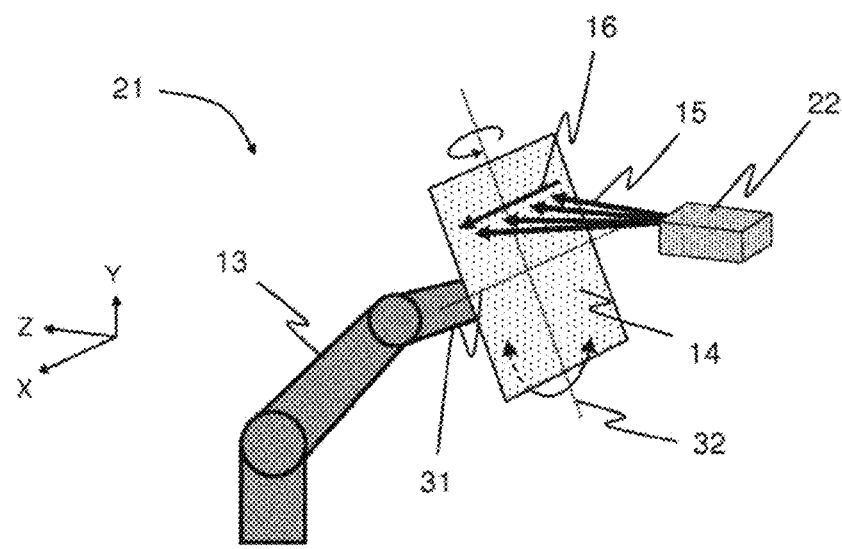
FIG. 3 is a schematic representation of the device according to a third aspect of the disclosed embodiment.

FIG. 3 illustrates one variant aspect that may apply to the two aspects FIGS. 1A, 1B, and 2.

According to this advantageous variant, applied, by way of example, to the aspect in FIGS. 1A and 1B, the handling arm 13 of the robot is configured so as to provide the part 14 with six degrees of freedom, and especially allows said part to be rotated around two perpendicular axes 31 and 32. Thus, the orientation of the part 14 relative to the laser source may be determined at any instant as a function of the zone illuminated by the laser beam 15 so that the illumination is at an optimal incidence, in particular taking into account the surface finish of the part 14 in the zone in question.

Such a configuration thus makes it possible to optimally orientate the part and rapidly scan a line by rotating the mirror allowing the deflection of the beam.

Regarding the variant aspects corresponding to FIGS. 1A to 3, will be noted that, in the case of inspection of a large part, it may be that the scan of the laser beam will not be sufficient to completely cover the part in the scanning direction. In this case, however, the part may be inspected sector by sector, a sector corresponding to a portion of the surface of the part defined by the amplitude of the scan and by the movement of the part along the axis perpendicular to the scanning axis. Thus, the part may be completely inspected by dividing the surface of the part into contiguous sectors explored one after the other.

Figure 4:
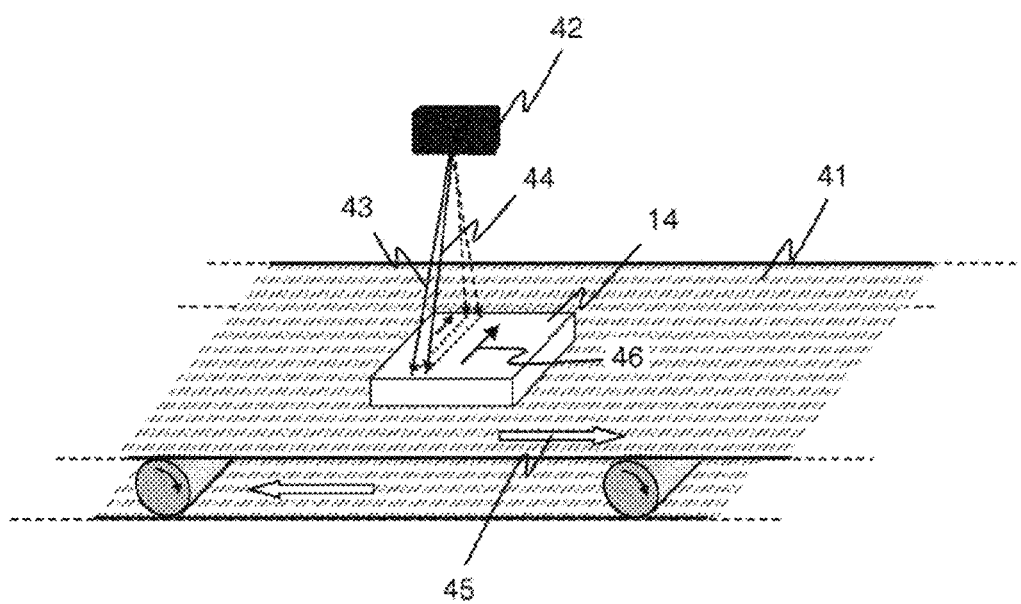
FIG. 4 is a schematic representation of the device according to a fourth aspect of the disclosed embodiment.

FIG. 4, for its part, illustrates a more particular aspect, the description of which will allow the advantageous character of the operating principle of the presently disclosed embodiment, especially in terms of rapidity of execution, to be illustrated. This aspect is more particularly suitable for inspecting the integrity of parts 14 that have one dimension that is larger than the others, for example elongate elements having a cross section that is small compared to their length.

This aspect is also advantageously applicable to the inspection of parts of relatively small size that are mass produced, the device then being placed at the end of the manufacturing line.

In this aspect, the handling robot of the device according to the presently disclosed embodiment consists of a mechanical translating element 41, a conveyor belt for example, on which the parts 14 to be inspected are placed, each part being placed on the belt in such a way that its length is oriented in the movement direction. The conveyor belt is associated with means allowing the belt to run, so that a part 14 that is deposited thereon may be moved so as to be illuminated by the laser beam of the inspecting head 42, the latter here being placed above the belt.

In this aspect, the inspecting head 42 is preferably equipped with a laser source emitting two beams simultaneously, 43 and 44, said beams being able to be deflected in order to carry out a scan in a direction 46 perpendicular to the movement direction of the conveyor belt, represented by the arrow 45. The amplitude of the scan of the laser beams is defined so as to cover the entirety of the extent of the part along the scanning axis, the part itself here being able to move only along a single axis. Thus, to completely inspect a part, it is enough to bring the part 14 level with the inspecting head 42 by actuating the conveyor belt, then to move the part 14 stepwise facing the inspecting head 42, the length of the motional step being defined both by the desired resolution and by the spacing of the two laser beams 43 and 44. Once the inspection has terminated, the conveyor belt 41 may be run continuously and more rapidly so as to bring the following part to face the inspecting head 42.

It will be noted that the use of a conveyor belt as the mechanical translating element 41 is here considered by way of exemplary aspect. Any element ensuring a translational movement of the parts 14 relative to the inspecting head 12 may obviously be envisioned in the context of the presently disclosed embodiment: translational tray, conveyor belt, rail, etc.

It will also be noted that regarding the latter exemplary aspect of the device according to the presently disclosed embodiment, the use of a handling robot consisting in a rectilinear mechanical translating element may be extended to the use of a mechanical element inducing a rotation of the inspected part. The handling robot then takes the form of a disk at the center of which the inspected part is deposited so that the latter, turning about itself, successively presents a plurality of faces to the laser beam of the inspecting head. Such a configuration is advantageously suitable for the inspection of parts having a certain rotational symmetry.

As will be apparent from the above description of the various exemplary aspects, the device according to the presently disclosed embodiment thus comprises, advantageously, two distinct means that interact to ensure a complete and rapid inspection of the part to be inspected.

The first means consists of a laser source equipped with means allowing the emitted laser beam(s) 15, 23-24, 43-44 to be deflected along a given scanning axis 16, 17 or 46.

The second means consists of a handling robot 13 that allows the part 14 to be inspected to be moved relative to the inspecting head, 12, 22 or 42, at least in a direction substantially perpendicular to the scanning axis, thereby avoiding use of a mobile inspecting head.

Thus, by combining the movements engendered by these two means, it is possible to rapidly inspect the entirety of the part in question without having to move the inspecting head itself. Such a configuration proves to be very advantageous in particular when the laser beams used are not compatible with fiber-optic transmission, and their implementation in the context of an inspecting head requires a more expensive and more complex opto-mechanic architecture.

Moreover, the combination of these means with means allowing the part to be rotated relative to the inspecting head advantageously makes it possible to obtain, for each inspection point, an optimal incidence of the laser beam relative to the surface of the inspected part.

What is claimed is:

1. A device for inspecting the structure of a composite part by laser ultrasound, comprising:
   an inspecting head including a source emitting at least one laser beam;
   a handling robot configured to hold a part and move a surface of said part relative to the inspecting head in such a way that said surface is able to be scanned by the at least one laser beam emitted by the source with which the inspecting head is equipped, said source including means for carrying out a scan of the at least one laser beam;
   means allowing the at least one laser beam to be deflected along a single scanning axis, so as to perform a mono-axial scan,
   wherein the scan is carried out along the scanning axis with a scanning amplitude, wherein the handling robot is configured to move the surface of the part along an axis substantially perpendicular to the scanning axis along which the scan of the at least one laser beam moves, and wherein the movement of the part is synchronized with a scanning of the at least one laser beam along the scanning axis during the scan.

2. The device as claimed in claim 1, wherein the source emits two laser beams and comprises means for scanning the two laser beams which allow the two laser beams to be scanned along two parallel axes.

3. The device as claimed in claim 2, wherein the means for scanning the two laser beams are configured so that each of the two laser beams is scanned independently of the other.

4. The device as claimed in claim 1, wherein the handling robot is configured in such a way that after each scan by the source, the surface of the part is moved relative to the inspecting head in such a way that the following scan covers a zone of the surface of the part as yet not scanned thereby.

5. The device claimed in claim 4, wherein a stepwise movement, d', of the part after each scan and a separation between the two laser beams is defined so as to obtain a complete scan of the surface of the part with a desired resolution.

6. The device as claimed in claim 1, wherein the handling robot includes means for gripping the part, which means for gripping the part are capable of making the surface of the part pivot about two substantially perpendicular axes.

7. The device as claimed in claim, 1, wherein the handling robot includes a translating element on which the part to be inspected is placed and ensuring a linear movement of the part, said element being arranged relative to the inspecting head in such a way that the part to be inspected moves along an axis substantially perpendicular to the scanning axis of the at least one laser beam.

8. The device as claimed in claim 7, wherein the handling robot is configured in such a way that during an inspection operation the part to be inspected can be brought, via a continuous movement of the translating element, into proximity with the inspecting head, then moved stepwise between two successive scans under the source.

9. The device as claimed in claim 1, wherein the handling robot includes a rotating element on which the part to be inspected is placed and allowing a rotation of the part, said element being arranged relative to the inspecting head in such a way that a plurality of faces of the part to be inspected are scanned in succession by the at least one laser beam of the inspecting head.

* * * * *